(12) United States Patent
Pepper et al.

(10) Patent No.: US 9,446,223 B2
(45) Date of Patent: Sep. 20, 2016

(54) METHOD OF MAKING A BALLOON DILATION CATHETER SHAFT HAVING END TRANSITION

(71) Applicant: BARD PERIPHERAL VASCULAR, INC., Tempe, AZ (US)

(72) Inventors: Lanny R. Pepper, Larue, TX (US); Charles J. Cox, Eustace, TX (US); William F. Davies, Jr., Athens, TX (US)

(73) Assignee: BARD PERIPHERAL VASCULAR, INC., Tempe, AZ (US)

( * ) Notice: Subject to any disclaimer, the term of this patent is extended or adjusted under 35 U.S.C. 154(b) by 435 days.

(21) Appl. No.: 13/939,478

(22) Filed: Jul. 11, 2013

(65) Prior Publication Data
US 2013/0333836 A1 Dec. 19, 2013

Related U.S. Application Data

(62) Division of application No. 12/355,659, filed on Jan. 16, 2009, now Pat. No. 8,728,110.

(51) Int. Cl.
| | | |
|---|---|---|
| *B29C 65/02* | (2006.01) | |
| *A61M 25/10* | (2013.01) | |
| *A61M 25/00* | (2006.01) | |
| *B29C 65/68* | (2006.01) | |
| *B29C 65/00* | (2006.01) | |
| *B29K 77/00* | (2006.01) | |
| *B29K 101/12* | (2006.01) | |
| *B29L 31/60* | (2006.01) | |
| *B29L 31/00* | (2006.01) | |
| *B29C 65/48* | (2006.01) | |

(Continued)

(52) U.S. Cl.
CPC ..... *A61M 25/1034* (2013.01); *A61M 25/0032* (2013.01); *A61M 25/104* (2013.01); *A61M 25/1006* (2013.01); *A61M 25/1025* (2013.01); *A61M 25/1036* (2013.01); *B29C 65/02* (2013.01); *B29C 66/5344* (2013.01); *B29C 66/53241* (2013.01); *A61M 25/0045* (2013.01); *A61M 25/0054* (2013.01); *B29C 65/08* (2013.01); *B29C 65/16* (2013.01); *B29C 65/18* (2013.01); *B29C 65/48* (2013.01); *B29C 65/483* (2013.01); *B29C 65/68* (2013.01); *B29C 66/004* (2013.01); *B29C 66/63* (2013.01); *B29K 2077/00* (2013.01); *B29K 2101/12* (2013.01); *B29L 2031/603* (2013.01); *B29L 2031/7542* (2013.01)

(58) Field of Classification Search
None
See application file for complete search history.

(56) References Cited

U.S. PATENT DOCUMENTS 5,879,499 A * 3/1999 Corvi ............... A61M 25/0012
156/173
6,013,190 A * 1/2000 Berg ................ A61M 25/0009
216/34

(Continued)

*Primary Examiner* — Edmund Lee
(74) *Attorney, Agent, or Firm* — King & Schickli, PLLC

(57) ABSTRACT

A catheter includes a balloon and a shaft having a coaxial portion including an outer tubular member having a bore, a transition neck, an access fitting adjacent the proximate end of the catheter shaft for directing a guidewire into the catheter shaft, an inflation port, a guidewire tubular member disposed coaxially in the outer tubular member, the outer tubular member and guidewire tubular member defining a first, annular inflation/deflation lumen fluid communication with the inflation port, at least one second inflation/deflation lumen separate from and non-coaxial with the guidewire tubular member and having a cross-sectional area less than the cross-sectional area of the first inflation/deflation lumen and opening at a proximate end into the first inflation/deflation lumen and at the distal end of the transition neck.

12 Claims, 4 Drawing Sheets

(51) Int. Cl.
*B29C 65/08* (2006.01)
*B29C 65/16* (2006.01)
*B29C 65/18* (2006.01)

(56) References Cited

U.S. PATENT DOCUMENTS 6,582,536 B2 * 6/2003 Shimada ........... A61M 25/0147
148/519

2003/0105427 A1 * 6/2003 Lee ................... A61M 25/1036
604/103.04
2004/0039332 A1 * 2/2004 Kantor .............. A61M 25/0023
604/103.04
2005/0113804 A1 * 5/2005 von Lehe ................ A61F 2/013
604/528
2015/0306806 A1 * 10/2015 Dando .............. A61M 25/0009
264/515

* cited by examiner

METHOD OF MAKING A BALLOON DILATION CATHETER SHAFT HAVING END TRANSITION

This application is a DIVISIONAL of U.S. patent application Ser. No. 12/355,659, filed Jan. 16, 2009 now U.S. Pat. No. 8,728,120, and titled "Balloon Dilation Catheter Shaft Having End Transition," the disclosure of which is incorporated by reference.

TECHNICAL FIELD

The disclosure relates to inflatable catheters and, specifically, to balloon dilation catheters. In particular, it relates to a balloon dilation catheter having a catheter shaft including a coaxial portion and a transition neck with one or more lumens formed through the transition neck.

BACKGROUND

Medical treatments using balloon dilation catheters, for example, Percutaneous Transluminal Angioplasty, have evolved to the point where such treatments require the insertion of catheters into narrower and more remote blood vessels within the body. This evolution has required the use of catheters having correspondingly smaller shaft diameters and longer shaft lengths. The migration toward catheters with smaller diameter longer shafts presents several challenges, not the least of which is catheter balloon inflation/deflation rates. As will be appreciated, as the diameter of catheter shafts has decreased the cross-sectional area available for inflation/deflation lumens has decreased. As the length of catheter shafts has increased, the pressure drop along the length of the inflation/deflation lumen or lumens has also increased. Hence, the amount of time required to inflate or deflate catheter balloons has increased as the diameter of catheter shafts has decreased and the lengths of such shafts has increased.

One conventional design for balloon dilation catheters is a coaxial design wherein two concentrically disposed tubular members form the catheter shaft. The bore of the inner tubular member forms the guidewire lumen with the outer tubular member forming the catheter shaft body. The annular space between the outer surface of the inner tubular member and the inner surface of the outer tubular member forms an inflation/deflation lumen for transporting an inflation medium such as a noncompressible fluid to inflate and deflate the dilation balloon. The inflation/deflation performance of a coaxial catheter is determined by the difference in cross-sectional area between the inside diameter of the outer tubular member and the outside diameter of the inner tubular member along with the length of the catheter shaft. For a given combination of catheter diameter and guidewire lumen diameter, the coaxial design is considered to maximize the cross-sectional area available for the inflation/deflation lumen thereby providing the best inflation/deflation performance for a given catheter length.

The balloon of a catheter utilizing the coaxial design is fastened at its proximal end to the distal end of the outer tubular member. The distal end of the balloon is fastened to the inner tubular member. However, the outer tubular member is not mechanically attached to the inner guidewire tubular member, rather the inner tubular member floats free within the outer tubular member. When inflated, the balloon may tend to elongate rather than expand in a radial direction since the distal end of the balloon is attached to the inner tubular member which may move longitudinally relative to the outer tubular member. The tendency to elongate detracts from the inflation performance of the balloon and additionally, places additional stresses on the joints where the proximal end of the balloon is attached to the outer tubular member and where the distal end of the balloon is attached to the guidewire tubular member.

Other conventional catheter designs utilize non-coaxial and separate guidewire and inflation lumens. These non-coaxial designs are referred to as "multi-lumen" catheters even though it is appreciated that coaxial designs have multiple lumens as well. In keeping with industry practices, for the purpose of this application, the term "multi-lumen" refers to designs wherein the guidewire lumen and inflation/deflation lumens are not coaxial. There are at least two types of multi-lumen catheter shafts: dual lumen shafts and extruded dual port shafts. In dual lumen shafts, a first tubular member forming the guidewire lumen therewithin and a second tubular member forming the inflation/deflation lumen therewithin run parallel to one another within a full diameter outer jacket surrounding both lumens. Since only the guidewire lumen member and the inflation/deflation lumen member (i.e., not the outer jacket) are exposed to the balloon inflation pressure, only these relatively small diameter tubular members need to be strong enough to withstand such pressures, and the full-diameter outer jacket of the catheter can be made of a softer and/or thinner material.

The other type of multi-lumen catheter, i.e., the extruded dual port shaft has guidewire and inflation/deflation lumens that are integrally formed longitudinal voids created during extrusion of the plastic or resin catheter shaft. The extrusion process enables construction of the catheter shaft and the lumens in non-circular geometries such as semi-circular or crescent. However, for the same diameter, or cross sectional area, the geometry of extruded dual port shafts and dual lumen shafts is inferior to the coaxial design in terms of inflation/deflation performance.

Hence, while multi-lumen shaft designs may present several advantages such as improved trackability, the cross-sectional configuration of such catheter shafts result in inflation/deflation performance that is inferior to that of coaxial shafts.

Thus, there exists a need for a balloon catheter having a shaft with inflation/deflation performance similar to that of a conventional coaxial design without the disadvantages thereof.

SUMMARY

In one aspect thereof, a shaft for a balloon dilation catheter to be utilized with a guidewire includes a catheter shaft having a coaxial portion including an outer tubular member having a bore, a proximate end, a distal end and a transition neck formed at the distal end of the coaxial portion. The transition neck has a proximate end at the distal end of the outer tubular member and a distal end remote from the distal end of the outer tubular member. The shaft further includes an access fitting adjacent the proximate end of the catheter shaft with an access port for directing a guidewire into the catheter shaft and an inflation port for directing an incompressible inflation medium into the catheter shaft.

The catheter shaft includes a guidewire tubular member having a bore defining a guidewire lumen, a proximate end and a distal end. The guidewire tubular member is disposed coaxially in the outer tubular member between the access port of the catheter shaft and extends continuously through the outer tubular member to the distal end of the outer tubular member and through the transition neck. The outer tubular member and guidewire tubular member define a first, annular inflation/deflation lumen therebetween in fluid communication with the inflation port, the first inflation/deflation lumen having a first cross section and terminating at the transition neck.

At least one second inflation/deflation lumen is formed through the transition neck. The second inflation/deflation lumen is separate from and non-coaxial with the guidewire tubular member and has a cross-sectional area less than the cross-sectional area of the first inflation/deflation lumen. The second inflation/deflation lumen opens at a proximate end thereof into the first inflation/deflation lumen and at the distal end of the transition neck, providing fluid communication from the first inflation/deflation lumen through the transition neck such that inflation fluid passing through the first inflation lumen may flow though the second inflation/deflation lumen and directly into a dilation balloon attached to the transition neck to inflate or deflate the dilation balloon.

In another aspect, the outer tubular member and the guidewire tubular member are formed from thermoplastic weldable materials such as nylon and polyether block amide and the neck transition is formed by welding the outer tubular member to the guidewire tubular member. One or both of the guidewire tubular member and outer tubular member may be loaded with sufficient bismuth to make the catheter shaft at least partially radiopaque.

In one variation, the distal end of the transition neck is adapted for connection to a proximal end of a dilation balloon, and the portion of the guidewire tubular member extending beyond the transition neck is adapted to pass through the interior of the dilation balloon and to be connected to a distal end of the balloon.

In another aspect, a method of making a balloon catheter includes positioning a guidewire tubular member in the bore of an outer tubular member such that the guidewire tubular member extends beyond the distal end of the outer tubular member. In one variation, the outer tubular member and inner tubular member are formed from weldable thermoplastic materials and the inner tubular member has a bore defining a guidewire lumen. An annular space between the outside surface of the guidewire tubular member and the inside surface of the outer tubular member defines a first inflation/deflation lumen.

A first mandrel is placed into the bore of the guidewire tubular member adjacent the distal end of the outer tubular member. At least one second mandrel is placed into the annular space between the guidewire tubular member and the outer tubular member adjacent the distal end of the outer tubular member. The outer tubular member and inner tubular member are heated to weld the outer tubular member to the guidewire tubular member at the distal end of the outer tubular member to form a transition neck whereby the thermoplastic materials of the outer tubular member and inner tubular member are bonded around the second mandrel. In one variation, the outer tubular member is welded to the guidewire tubular member by compression thermal molding. A heat shrink material such as a PTFE tube may be placed around the distal end of outer tubular member and the guidewire tubular member prior to heating the outer tubular member and guidewire tubular member.

The second mandrel is removed from the transition neck to form a second inflation/deflation lumen that extends from the first inflation/deflation lumen and opens at the distal end of the transition neck. A proximal end of a dilation balloon is attached to the transition neck and the distal end of the dilation balloon is likewise attached to the guidewire tubular member. The balloon may be attached to the outer tubular member and guidewire tubular member by welding or gluing.

In one variation, the balloon is placed over the guidewire tubular member with a proximate end of the balloon adjacent the distal end of the outer tubular member prior to welding the outer tubular to the guidewire tubular member. The proximate end of the balloon, the outer tubular member and guidewire tubular member are heated to weld the proximate end of the balloon, the outer tubular member and guidewire tubular member together to form the transition neck. The proximate end of the balloon, the outer tubular member and guidewire tubular member may be welded together using compression thermal molding.

BRIEF DESCRIPTION OF THE DRAWINGS

For a more complete understanding, reference is now made to the following description taken in conjunction with the accompanying Drawings in which.

DETAILED DESCRIPTION

Figure 1:
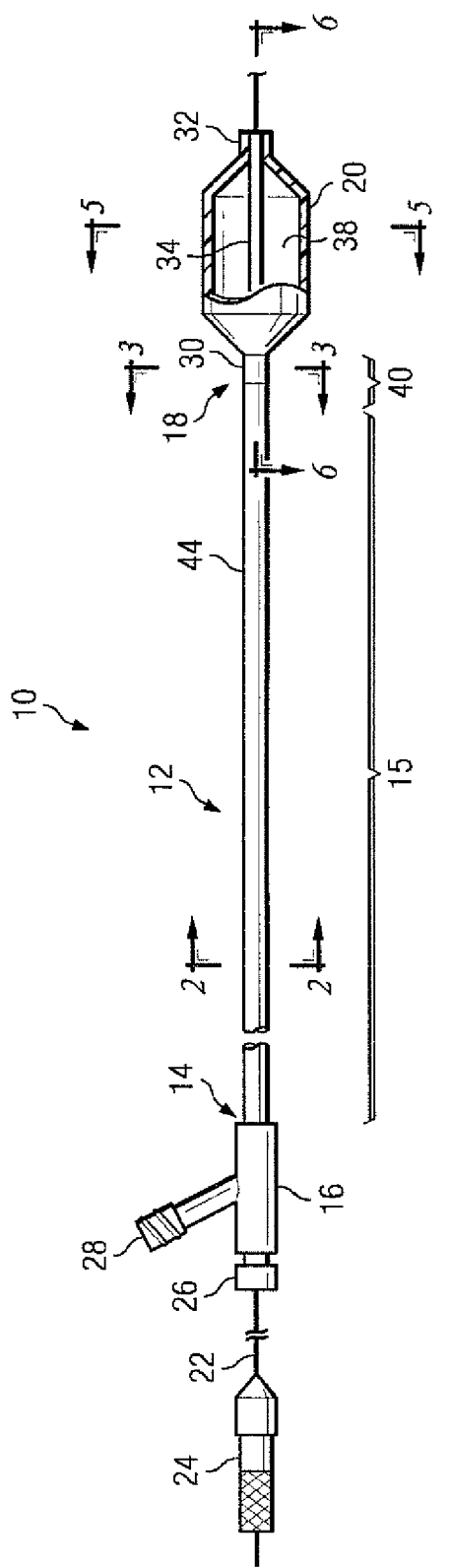
FIG. 1 is a side view of a balloon dilation catheter according to the disclosure.

This application incorporates by reference the disclosures of pending U.S. patent application Ser. No. 11/158,855, published as US2007-0010847A1, and pending U.S. patent application Ser. No. 11/174,676, published as US2007-0016133A1.

Referring now to the drawings, wherein like reference numbers are used herein to designate like elements throughout, the various views and embodiments of a balloon dilation catheter shaft having an end transition are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Turning now to FIG. 1, in one embodiment a balloon dilation catheter 10 includes a shaft 12 having a proximate end 14 and a distal end 18. As set forth in detail below, a plurality of tubular members disposed in catheter 10 define internal, longitudinally extending passages known as lumens. In one variation, the tubular members are formed from weldable thermoplastic materials and one or more of the tubular members may include a material, such as bismuth, for radiopacity.

Referring still to FIG. 1, one tubular member, the guidewire tubular member, extends longitudinally through the catheter from access fitting 16 to the distal end 32 of dilation balloon 20. The guidewire tubular member 34 has a bore defining a guidewire lumen through which a conventional guidewire 22 may be directed through the interior of catheter 10. Access fitting 16 is attached to proximate end 14 of shaft 12. As illustrated, access fitting 16 includes a first port 26 for receiving a guidewire 22 therethrough and directing guidewire 22 into the guidewire lumen in shaft 12. Access fitting 16 includes a second port 28 adapted to receive an incompressible inflation medium and direct the medium into an inflation/deflation lumen in shaft 12. Guidewire 22 may be provided with a manipulator 24 for rotating and positioning the guidewire from the proximal end of catheter 10.

Referring still to FIG. 1, a dilation balloon 20 is affixed to the distal end 18 of shaft 12. Balloon 20 may be of conventional construction and is typically formed of relatively non-distensible plastic or polymer material such as nylon. The envelope of the balloon may be plain or reinforced with filaments or fibers. For the purpose of illustration, balloon 20 is shown in an inflated configuration in FIG. 1 with portions of the envelope broken away to better illustrate the interior structure of the balloon. While balloon 20 is illustrated in an inflated configuration, it will be appreciated that when deflated the balloon can typically be folded in such a manner as to have an outside diameter or cross section approximately equal to that of catheter shaft 12. The dimensions of balloon 20 may also vary significantly from that illustrated in FIG. 1 both radially and longitudinally.

Balloon 20 may be attached to distal end 18 of shaft 12 using various techniques known in the art. In the embodiment illustrated in FIG. 1, the proximate end 30 of balloon 20 is welded to shaft 12 as will be described in detail below. In other embodiments, the proximal end 30 of balloon 20 may be connected to shaft 12 of catheter 10 by means of a medical grade epoxy adhesive. The distal end 32 of balloon 20 is connected with a fluid-tight seal to the outside (i.e. radial) surface of guidewire tubular member 34, which, as illustrated, extends beyond the distal end of the catheter shaft, passing through the interior of balloon 20. In one variation, the distal end 32 of balloon 20 is welded to guidewire tubular member 34 in order to form a fluid-tight seal. In other variations, the distal end 32 of balloon 20 may be adhered to guidewire tubular member 34 by means of a medical grade epoxy. In still other variations, a thermoplastic shim (not shown) may be placed between the distal end of tubular guidewire member 34 and the distal end of balloon 32 in order to provide material from which the distal end of catheter 10 may be molded to provide a desired configuration or profile.

In order to obtain relatively high inflation/deflation rates, catheter shaft 12 is formed with a coaxial portion 15 and a transition neck 40. Coaxial portion 15 extends between access fitting 16 and transition neck 40. Within coaxial portion 15, guidewire tubular member 34 defines a guidewire lumen while outer tubular member 44 defines an inflation/deflation lumen between the inside surface of the outer tubular member and the outside surface of the guidewire tubular member. Outer tubular member 44 and guidewire tubular member 34 may be formed from a variety of suitable plastic materials. In the embodiment illustrated in FIG. 1, guidewire tubular member 34 and outer tubular member 44 are formed from weldable thermoplastic materials such as nylon-11, nylon-12 and/or a polyether block amide (PEBA). In one embodiment, guidewire tubular member 34 and/or outer tubular member 44 may be formed from PEBA elastomers sold under the trademark Pebax®. PEBA elastomers are available in plastizer and additive-free medical grades having a nominal hardness (Shore D) from about Shore D 30 to about Shore D 72. The thermoplastic materials used to make tubular guidewire member 34 and outer tubular member 44 may be loaded with materials such as carbon nanotubes or similar materials in order to enhance the strength of the tubular members. In other variations, tubular guidewire member 34 and/or outer tubular member 44 may be loaded with a radialopaque material such as bismuth. In one variation, tubular guidewire member 34 and/or tubular outer member 44 may be loaded with up to approximately twenty percent by weight bismuth.

Figure 2:
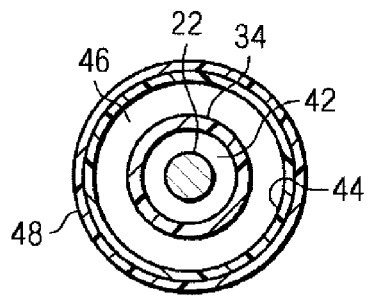
FIG. 2 is a first cross-section of the balloon dilation catheter shaft of FIG. 1 taken through a coaxial portion thereof.

FIG. 2 is a cross-section of catheter shaft 12 taken through coaxial portion of the shaft. As illustrated, tubular guidewire member 34 defines a guidewire lumen 42 through which guidewire 22 passes. Outer tubular member 44 defines an inflation/deflation lumen 46 between the inside surface of the outer tubular member and the outside surface of the guidewire tubular member through which an incompressible fluid may be directed to inflate or deflate balloon 20. In one variation, an outer coating 48 may be applied to outer tubular member 44 to enhance the properties of catheter 10. For example, coating 48 may be a radiopaque material to enhance the visibility of catheter shaft 12 by means of radiography. Alternatively, coating 48 may be made of a material that provides a smooth exterior surface to minimize the tendency of blood cells to accumulate and/or of a hydrophilic material that exhibits lubricity in contact with blood. As will be appreciated, the flexibility of catheter shaft 12 may be varied along the length of the shaft by varying the wall thicknesses of tubular guidewire member 34 and/or outer tubular member 44 or by varying the composition of the materials from which the tubular guidewire member and outer tubular member are formed.

Figure 3:
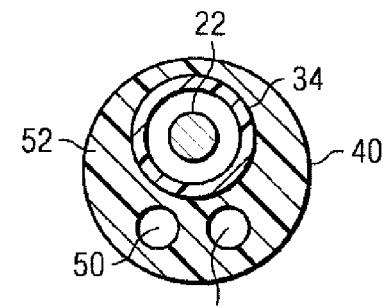
FIG. 3 is a second cross-sectional view of the balloon catheter shaft of FIG. 1 taken through the neck transition of the catheter.

FIG. 3 is a cross-section of catheter shaft 12 taken through transition neck 40. As illustrated, transition neck 40 includes one or more secondary inflation/deflation lumens 50. Secondary lumens 50 extend from inflation/deflation lumen 46 of coaxial portion 15 of catheter shaft 12 through transition neck 40, opening into balloon 20. Secondary lumens 50 are formed by inserting a mandrel or mandrels between outer tubular member 44 and guidewire tubular member 34 prior to forming transition neck 40. A mandrel is also positioned within guidewire tubular member 34 in the region of neck 40 prior to forming the neck to prevent obstruction of guidewire lumen 42. In one variation, transition neck 40 may be formed by means of thermal compression molding as described below.

Referring still to FIG. 3, in one variation, tubular guidewire member 34 is positioned in outer tubular member 44 and mandrels are inserted between the guidewire tubular member and outer tubular member to form secondary inflation/deflation lumens 50. A mandrel is also inserted into guidewire tubular member 34 to prevent the guidewire tubular member from collapsing during the molding process. The mandrels may be formed from a variety of materials for example, stainless steel or PTFE so long as the mandrels have sufficient mechanical strength and thermal resistance to withstand the heat and pressure of the molding process. In one variation, a heat shrink material such as a Teflon (PTFE) film or tube is placed around catheter shaft 12 in the region where transition neck 40 is to be formed.

To form the transition neck, the region of transition neck 40 of catheter shaft 12 is heated to a temperature above the softening point of the thermoplastics from which outer tubular member 44 and guidewire tubular member 34 are formed, typically between 300 degrees Fahrenheit and 400 degrees Fahrenheit. Heating the transition neck region 40 may be accomplished in a number of different ways. For example, the transition neck region 40 may be placed in a heated die. Alternatively, the transition neck region 40 may enclosed in a heat shrink material and heated in a small oven. Alternatively, the transition neck region may be heated ultrasonically or with a laser. If a heated die is used, it may not be necessary to use a heat shrink material since the die may be configured to compress the transition neck region during the heating process.

Upon heating, the softened thermoplastic materials tend to flow together around the mandrels to form secondary inflation/deflation lumens 50. In a variation wherein a heat shrink material is used, the heating process causes the heat shrink material to shrink, compressing the softened thermoplastic materials together. Compression molding using a heat shrink material tends to eliminate irregularities or discontinuities in the surface of transition neck 40. During the thermal compression molding process, the thermoplastic materials from which the inner tubular member 34 and outer tubular member 44 are formed flow or bond together to form a continuous mass 52 that surrounds secondary inflation/deflation lumens 50 and guidewire lumen 42 when the mandrels are removed. In one variation mass 52 forms a fluid tight bond with guidewire tubular member 34 that mechanically attaches the guidewire tubular member to the outer tubular member. Notably, secondary inflation/deflation lumens 50 are formed without the use of additional tubes or hollow members.

Figure 4:
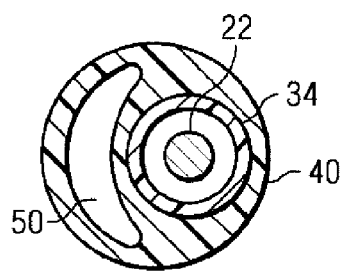
FIG. 4 is a cross-section through the neck transition of the catheter illustrating an alternative lumen configuration.

Multiple secondary inflation/deflation lumens 50 may be formed during the thermal compression molding process. In the variation illustrated in FIG. 3, two secondary inflation/deflation lumens having a circular cross-section are formed. In other variations, different numbers of secondary lumens and/or different geometries may be used. For example, the cross-section of secondary inflation/deflation lumens 50 could be square, triangular or polygonal. In the variation illustrated in FIG. 4, the cross-section of secondary inflation/deflation lumen 50 is crescent shaped. As will be appreciated, the geometry of inflation/deflation lumens will tend to match the outside profile of the mandrel or mandrels placed in the annular space between the guidewire tubular member and outer tubular member prior to heating.

Regardless of the particular geometry selected for secondary inflation/deflation lumen or lumens 50, the cross-sectional area of the secondary lumen or lumens will be less than the cross-sectional of inflation/deflation lumen 46 of the coaxial portion 15 of catheter shaft 12. Therefore, in order to minimize the pressure drop across transition neck 40, it is preferred to make the neck as short as possible. Generally, the length of transition neck 40 must be sufficient to provide a bond between outer tubular member 44 and guidewire member 34 having sufficient mechanical strength to resist delamination under pressure. Further, the length of transition neck 40 should be sufficient to compensate for any material defects. Typically, the length of transition neck 40 will be less than 10 mm. In some variations, the length of transition neck 40 may be in the range of 2-4 mm.

Figure 5:
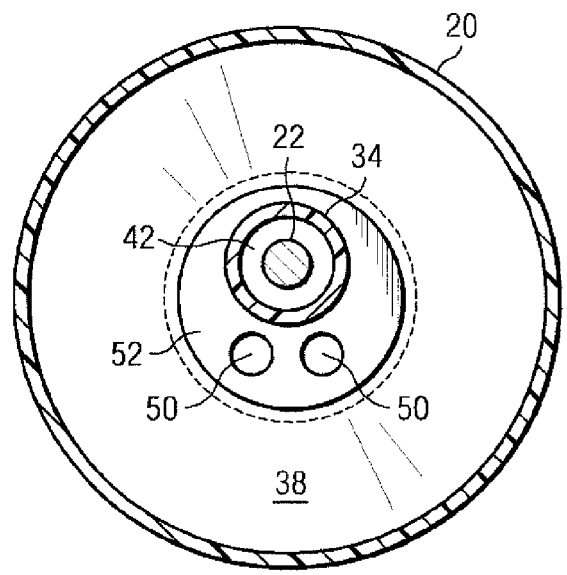
FIG. 5 is a cross-section of the catheter of FIG. 1 taken through the balloon of the catheter.

FIG. 5 is a cross-section of dilation catheter 10 taken through balloon 20 in a direction toward the proximal end of the catheter. In one variation, balloon 20 is also formed from a thermoplastic material such as PEBA, nylon-11 or nylon-12. In this variation, balloon 20 may be welded onto catheter shaft 12 during the compression molding process wherein transition neck 40 is formed. Balloon 20 is positioned over guidewire tubular member 34 prior to the thermal compression molding process with proximal end 30 in abutting relationship with the distal end of outer tubular member 44. The region of transition neck 40 is then welded by means of thermal compression molding as previously described. The use of a heat shrink material in this process causes the thermoplastic material of balloon 20 to soften and flow together with the thermoplastic guidewire tubular member 34 and outer tubular member 44. Line 54 in FIG. 5 represents the proximal end 30 of balloon 20 in abutting relationship with the distal end of outer tubular member 44.

As will be appreciated, transition neck 40 could also be formed by a gluing process using, for example, a medical grade epoxy. In this case, mandrels would be inserted between outer tubular member 44 and inner tubular member 34 as previously described to form secondary inflation/deflation lumens 50. An adhesive such as an epoxy would then be applied between the guidewire tubular member 34 and outer tubular 44 around the mandrels. Alternatively, an adhesive could be applied to the outer surface of guidewire tubular member 34 before outer tubular member 44 is placed over the guidewire tubular member. The outer tubular member 44 would then be positioned over guidewire tubular member 34 and mandrels inserted through the adhesive to form secondary inflation/deflation lumens 50. The proximal end 30 of balloon 20 would then be glued onto the distal end of shaft 12 with an adhesive such as an epoxy. While transition neck 40 could be formed with an adhesive, in some cases such a process may be more complicated and time consuming than thermal compression molding. However, if the outer tubular member 44 and/or guidewire tubular member 34 is fanned from a non-weldable material such as a metal or a polyimide it may be necessary to form neck transition 40 with an adhesive. Likewise, if differences between the softening temperatures of the materials used to form guidewire tubular member 34 and outer tubular member 44 are too large to permit welding, neck transition 40 may be formed with an appropriate adhesive.

Figure 6:
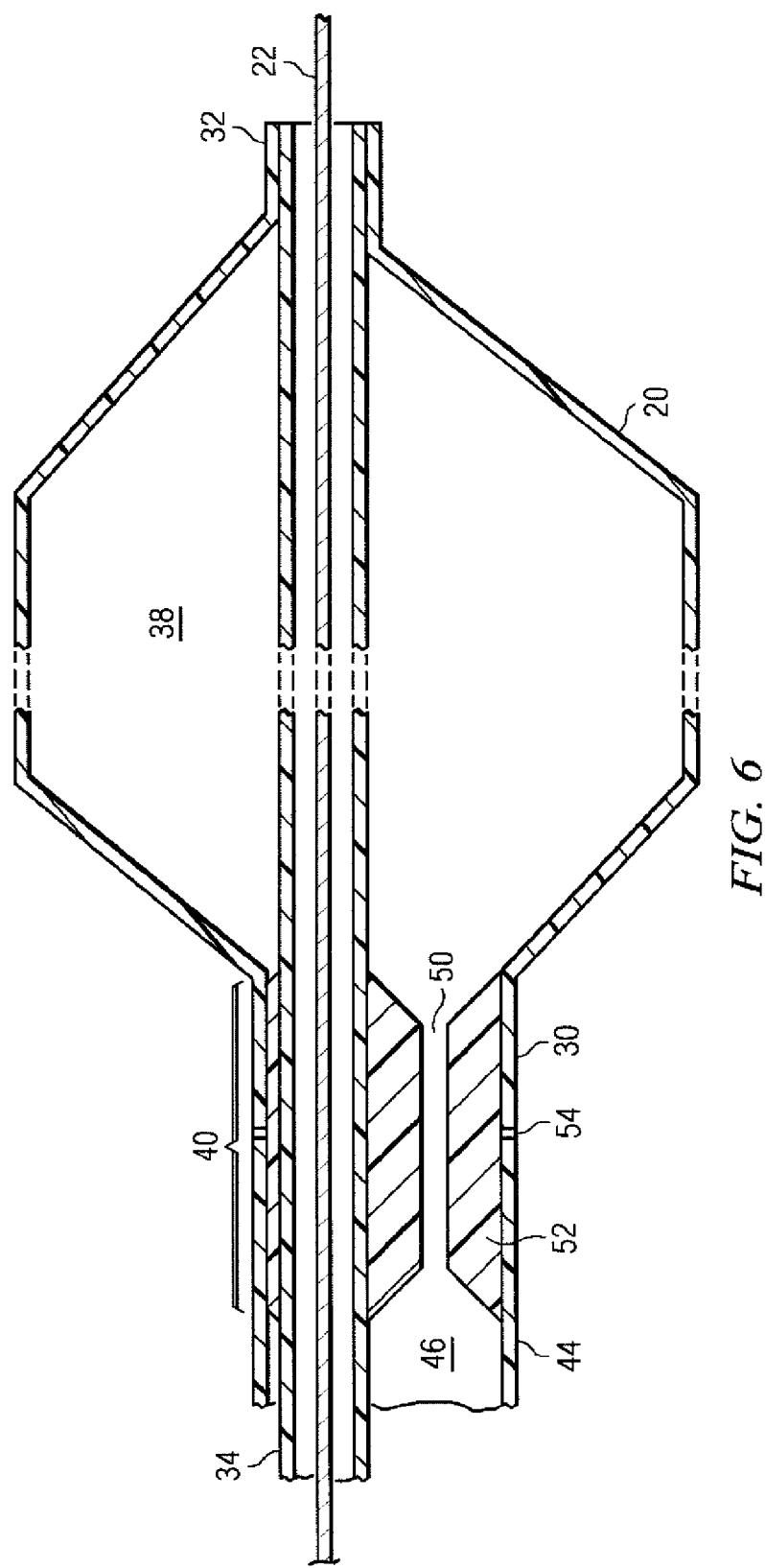
FIG. 6 is a longitudinal section of the balloon and transition neck of the catheter of FIG. 1.

FIG. 6 is a longitudinal section of catheter 10 taken through balloon 20 and transition neck 40. As illustrated, secondary inflation/deflation lumens 50 provide a passage between inflation/deflation lumen 46 of coaxial portion 15 of shaft 12 and the interior 38 of balloon 20. FIG. 6 also illustrates the melted together mass 52 of thermoplastic material surrounding secondary inflation/deflation lumens 50 and guidewire tubular member 34. Although the junction of the distal end of outer tubular member 44 and the proximal end 30 of balloon 20 is represented by a line 54 in FIGS. 5 and 6, it will be appreciated that after the thermal compression molding process, the thermoplastic materials will have fused together to form a continuous exterior surface through neck transition section 40.

Figure 7:
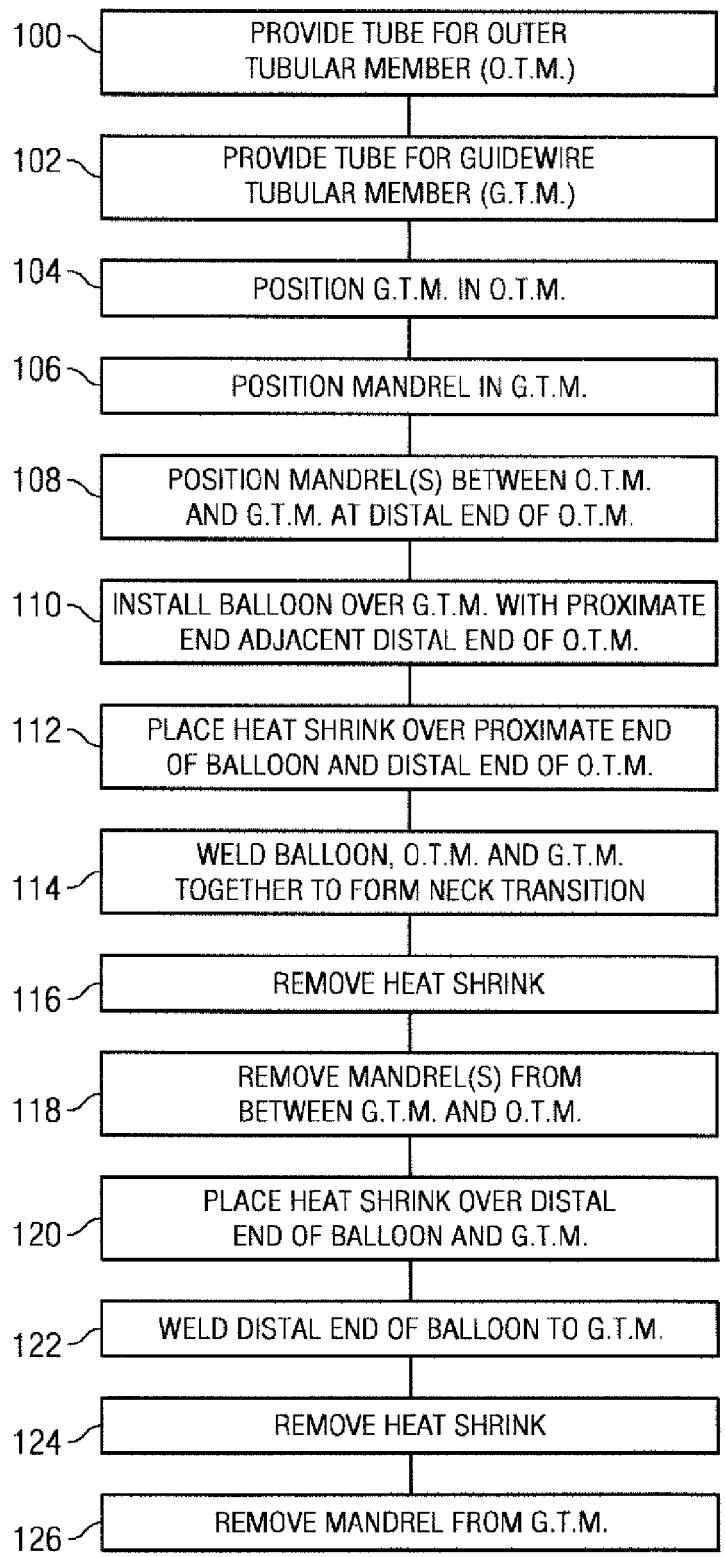
FIG. 7 is a flow chart of a method for constructing one embodiment of a catheter of the disclosure.

FIG. 7 is a block diagram illustrating a method of making catheter 10. In accordance with the method, the outer tubular member and guidewire tubular member are provided as steps 100 and 102. In this variation, neck transition 40 is formed by means of thermal compression molding; hence, the tubes are formed from a thermoplastic material such as nylon or PEBA. The outer tubular member is positioned over the guidewire tubular member at step 104. A mandrel is positioned in guidewire tubular member at step 106 to protect the guidewire tubular member from collapsing during the thermal compression molding process. At step 108, one or more mandrels are positioned between the outer tubular member and guidewire tubular member at the distal end of the outer tubular member. The mandrels are sufficiently long to extend through the area to be compression molded so as to form secondary lumens through the neck transition.

In this variation, at step 110 a balloon formed from a thermoplastic material is then positioned over the guidewire tubular member with the proximal end of the balloon in abutting relation with the distal of the outer tubular member. In other variations of the method, the balloon may be welded or glued to the transition neck after the guidewire tubular member and outer tubular member have been welded together to form the neck.

Heat shrink material is then positioned around the distal end of the outer tubular member and proximal end of the balloon in the area where the neck transition is to be formed at step 112. In one embodiment, the heat shrink material is provided in the form of a tube that is slipped over the distal end of the outer tubular member and proximal end of the balloon. At step 114 the distal end of the outer tubular member, the inner tubular member and the proximal end of the balloon are welded together by means of thermal compression molding. If the thermal compression molding process is accomplished using a heat shrink material, the region of the transition neck may then be heated by any convenient means. For example, the neck transition region could be heated in an oven, ultrasonically, in a heated die, or alternatively a laser could be used to heat the neck transition region. If heated die is used in the thermal compression molding process, the die may be configured to compress the neck transition region, eliminating the need for a heat shrink-wrapping.

After the thermal compression molding process is completed the heat shrink material is removed from the neck transition at step 116. The mandrels used to form the secondary lumens are then removed from the formed neck transition at step 118. The distal end of the balloon is then attached to the guidewire tubular member. In one variation, a shim formed from a thermoplastic material may be placed over the guidewire tubular member at the location where the distal end of the balloon is to be attached to the guidewire tubular member. In other variations, the distal end of the balloon attached directly to the guidewire tubular member. At step 120, a heat shrink material is placed over the distal end of the balloon and guidewire tubular member. The distal end of the balloon is then welded to the guidewire tubular member by thermal compression molding at step 122. The heat shrink material and guidewire tubular member are then removed at steps 124 and 126.

In one variation, the guidewire tubular member is placed under compression between the proximal and distal ends of the balloon. This accomplished by using a curved mandrel or member such as a piece of stainless steel wire to create an arc or bow in the portion of the guidewire tubular member within the balloon prior to welding the distal end of the balloon to the guidewire tubular member. After the distal end of the balloon is welded to the guidewire tubular member, the guidewire tubular member retains the arc under compression between the proximal and distal ends of the balloon. When the balloon elongates upon inflation, the arced portion of the guidewire tubular member will straighten. This in turn reduces the forces applied to the joints between the outer tubular member at the proximal end of the balloon and between the distal end of the balloon and the guidewire tubular member at the distal end of the balloon when the balloon is inflated. Reducing these forces tends to prevent delamination of the balloon from the guidewire tubular member and/or at the neck transition.

It will be appreciated by those skilled in the art having the benefit of this disclosure that the balloon dilation catheter shaft having end transition described herein provides a dilation catheter having improved inflation/deflation performance without the disadvantage inherent in the prior art. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A method of making a catheter comprising:
   positioning a first tubular member in the bore of a second tubular member, wherein the first tubular member has a bore defining a guidewire lumen and wherein an annular space between the first tubular member and the second tubular member defines a first inflation/deflation lumen;
   inserting at least one mandrel into the annular space between the first tubular member and the second tubular member;
   attaching the first tubular member to the second tubular member adjacent the mandrel to form a transition neck at a distal end of the second tubular member, wherein the attachment forms a bond around the mandrel; and
   removing the mandrel to form a second inflation/deflation lumen, the second inflation/deflation lumen in fluid communication with the first inflation/deflation lumen and opening at the distal end of the transition neck.

2. The method of claim 1, further including the step of attaching a dilation balloon to the catheter.

3. The method of claim 2, wherein a proximal end of the dilation balloon is attached to the transition neck with heat shrink material.

4. The method of claim 2, wherein a distal end of the first tubular member extends past as distal end of the second tubular member, and further including the step of attaching as distal end of the dilation balloon to the distal end of the first tubular member.

5. The method of claim 2, wherein a distal end of the balloon is attached to the first tubular member, and wherein the first tubular member is placed under compression between is proximal end of the balloon and the distal end of the balloon.

6. The method of claim 5, wherein a curved mandrel is placed in the first tubular member to create an arc in the first tubular member between the proximal and distal ends of the balloon.

7. The method of claim 1, wherein at least one of the first and second tubular members comprises a thermoplastic material.

8. The method of claim 7, wherein the attachment step comprises thermal compression molding the at least one of the first and second tubular members to the other of the first and second tubular members.

9. The method of claim 8, wherein the thermoplastic material forms the bond around the mandrel.

10. The method of claim 1, wherein the inserting step comprises inserting a plurality of mandrels into the annular space between the first and second tubular members, and the removing step comprises forming a plurality of second inflation/deflation lumens, each in fluid communication with the first inflation/deflation lumen.

11. The method of claim 1, further including the step of inserting a second mandrel in the first tubular member.

12. The method of claim 1, wherein the second inflation/deflation lumen is distal to the first inflation/deflation lumen.

* * * * *